US008626525B2

(12) United States Patent  
Mi et al.

(10) Patent No.: US 8,626,525 B2
(45) Date of Patent: Jan. 7, 2014

(54) SYSTEMS AND METHODS FOR REAL-TIME MONITORING AND ANALYSIS OF PRESCRIPTION CLAIM REJECTIONS

(75) Inventors: Zhe Cheng Mi, Lawrenceville, GA (US); Rita Sue Russell, Atlanta, GA (US)

(73) Assignee: McKesson Financial Holdings, Hamilton (BM)

( * ) Notice: Subject to any disclaimer, the term of this patent is extended or adjusted under 35 U.S.C. 154(b) by 511 days.

(21) Appl. No.: 12/144,293

(22) Filed: Jun. 23, 2008

(65) Prior Publication Data

US 2009/0319311 A1 Dec. 24, 2009

(51) Int. Cl.
*G06Q 10/00* (2012.01)

(52) U.S. Cl.
USPC .................................. 705/2; 705/3

(58) Field of Classification Search
USPC .......................................................... 705/2
See application file for complete search history.

(56) References Cited

U.S. PATENT DOCUMENTS

| | | | |
|---|---|---|---|
| 4,674,041 A | 6/1987 | Lemon et al. |
| 4,723,212 A | 2/1988 | Mindrum et al. |
| 4,910,672 A | 3/1990 | Off et al. |
| 5,007,641 A | 4/1991 | Seidman |
| 5,080,364 A | 1/1992 | Seidman |
| 5,173,851 A | 12/1992 | Off et al. |
| 5,201,010 A | 4/1993 | Deaton et al. |
| 5,235,702 A | 8/1993 | Miller |
| 5,237,620 A | 8/1993 | Deaton et al. |
| 5,301,105 A | 4/1994 | Cummings |
| 5,305,196 A | 4/1994 | Deaton et al. |
| 5,327,508 A | 7/1994 | Deaton et al. |
| 5,359,509 A | 10/1994 | Little et al. |
| 5,388,165 A | 2/1995 | Deaton et al. |
| 5,430,644 A | 7/1995 | Deaton et al. |
| 5,448,471 A | 9/1995 | Deaton et al. |
| 5,544,044 A | 8/1996 | Leatherman |

(Continued)

FOREIGN PATENT DOCUMENTS

| | | |
|---|---|---|
| CA | 2482370 A1 | 3/2006 |
| EP | 1310895 A2 | 11/2002 |

(Continued)

OTHER PUBLICATIONS

Non-Final Office Action for U.S. Appl. No. 12/164,898 mailed Dec. 16, 2010.

(Continued)

*Primary Examiner* — Hiep V Nguyen
(74) *Attorney, Agent, or Firm* — Sutherland Asbill & Brennan LLP

(57) ABSTRACT

Embodiments of the invention can provide systems and methods for real-time monitoring and analysis of prescription claim rejections. In one embodiment, a transaction performance monitoring system for facilitating real-time monitoring of the rejection of claims can be provided. The transaction performance monitoring system can include a transaction performance monitoring application operable to receive a plurality of claims associated with at least one dispenser, wherein each of the claims relates to at least one prescription and at least one payor. In addition, a transaction performance monitoring application operable to, in real-time, identify rejected claims and associated causes of the rejected claims. Furthermore, a transaction performance monitoring system can include a network operable to communicate the plurality of claims between the at least one dispenser and the at least one payor.

20 Claims, 7 Drawing Sheets

(56) References Cited

U.S. PATENT DOCUMENTS

| | | |
|---|---|---|
| 5,550,734 A | 8/1996 | Tarter et al. |
| 5,588,649 A | 12/1996 | Blumberg et al. |
| 5,592,560 A | 1/1997 | Deaton et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |
| 5,644,723 A | 7/1997 | Deaton et al. |
| 5,644,778 A | 7/1997 | Burks et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,704,044 A | 12/1997 | Tarter et al. |
| 5,748,907 A | 5/1998 | Crane |
| 5,749,907 A | 5/1998 | Mann |
| 5,832,447 A | 11/1998 | Rieker et al. |
| 5,832,457 A | 11/1998 | O'Brien |
| 5,845,255 A | 12/1998 | Mayaud |
| 5,857,175 A | 1/1999 | Day et al. |
| 5,892,827 A | 4/1999 | Beach et al. |
| 5,892,900 A | 4/1999 | Ginter et al. |
| 5,915,007 A | 6/1999 | Klapka |
| 5,926,795 A | 7/1999 | Williams |
| 5,950,169 A | 9/1999 | Borghesi et al. |
| 5,956,736 A | 9/1999 | Hanson et al. |
| 5,963,915 A | 10/1999 | Kirsch |
| 5,970,469 A | 10/1999 | Scroggie et al. |
| 5,974,399 A | 10/1999 | Giuliani et al. |
| 5,991,750 A | 11/1999 | Watson |
| 6,006,242 A | 12/1999 | Poole et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,073,104 A | 6/2000 | Field |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,208,973 B1 | 3/2001 | Boyer et al. |
| 6,224,387 B1 | 5/2001 | Jones |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,940 B1 | 10/2001 | Yamamoto et al. |
| 6,307,958 B1 | 10/2001 | Deaton et al. |
| 6,321,210 B1 | 11/2001 | O'Brien et al. |
| 6,324,516 B1 | 11/2001 | Shults et al. |
| 6,330,546 B1 | 12/2001 | Gopinathan et al. |
| 6,334,108 B1 | 12/2001 | Deaton et al. |
| 6,341,265 B1 | 1/2002 | Provost et al. |
| 6,343,271 B1 | 1/2002 | Peterson et al. |
| 6,351,735 B1 | 2/2002 | Deaton et al. |
| 6,377,935 B1 | 4/2002 | Deaton et al. |
| 6,424,949 B1 | 7/2002 | Deaton et al. |
| 6,427,020 B1 | 7/2002 | Rhoads |
| 6,484,146 B2 | 11/2002 | Day et al. |
| 6,584,448 B1 | 6/2003 | Laor |
| 6,632,251 B1 | 10/2003 | Rutten et al. |
| 6,671,692 B1 | 12/2003 | Marpe et al. |
| 6,671,693 B1 | 12/2003 | Marpe et al. |
| 6,684,195 B1 | 1/2004 | Deaton et al. |
| 6,698,013 B1 | 2/2004 | Bertero et al. |
| 6,714,918 B2 | 3/2004 | Hillmer et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,879,959 B1 | 4/2005 | Chapman et al. |
| 6,885,994 B1 | 4/2005 | Scroggie et al. |
| 7,013,284 B2 | 3/2006 | Guyan et al. |
| 7,024,374 B1 | 4/2006 | Day et al. |
| 7,058,584 B2 | 6/2006 | Kosinski et al. |
| 7,058,591 B2 | 6/2006 | Giuliani et al. |
| 7,111,173 B1 | 9/2006 | Scheidt |
| 7,155,397 B2 | 12/2006 | Alexander et al. |
| 7,225,052 B2 | 5/2007 | Foote et al. |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,356,460 B1 | 4/2008 | Kennedy et al. |
| 7,380,707 B1 | 6/2008 | Fredman |
| 7,401,027 B2 | 7/2008 | Moore et al. |
| 7,415,426 B2 | 8/2008 | Williams et al. |
| 7,418,400 B1 | 8/2008 | Lorenz |
| 7,426,480 B2 | 9/2008 | Granger et al. |
| 2001/0001014 A1 | 5/2001 | Akins, III et al. |
| 2001/0032099 A1 | 10/2001 | Joao |
| 2001/0037216 A1 | 11/2001 | Oscar et al. |
| 2001/0037224 A1 | 11/2001 | Eldridge et al. |
| 2001/0041993 A1 | 11/2001 | Campbell |
| 2002/0002495 A1 | 1/2002 | Ullman |
| 2002/0035488 A1 | 3/2002 | Aquila et al. |
| 2002/0044043 A1 | 4/2002 | Chaco et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0087554 A1 | 7/2002 | Seelinger |
| 2002/0087583 A1 | 7/2002 | Morgan et al. |
| 2002/0111832 A1 | 8/2002 | Judge |
| 2002/0120473 A1 | 8/2002 | Wiggins |
| 2002/0128883 A1 | 9/2002 | Harris |
| 2002/0133503 A1 | 9/2002 | Amar et al. |
| 2002/0138593 A1 | 9/2002 | Novak et al. |
| 2002/0175370 A1 | 11/2002 | Bockelman |
| 2002/0183979 A1 | 12/2002 | Wildman |
| 2002/0198831 A1 | 12/2002 | Patricelli et al. |
| 2003/0009357 A1 | 1/2003 | Pish |
| 2003/0009367 A1 | 1/2003 | Morrison |
| 2003/0028404 A1 | 2/2003 | Herron et al. |
| 2003/0050799 A1 | 3/2003 | Jay et al. |
| 2003/0069760 A1 | 4/2003 | Gelber |
| 2003/0074218 A1 | 4/2003 | Liff et al. |
| 2003/0074222 A1 | 4/2003 | Rosow et al. |
| 2003/0074345 A1 | 4/2003 | Baldwin et al. |
| 2003/0083903 A1 | 5/2003 | Myers |
| 2003/0120588 A1 | 6/2003 | Dodd et al. |
| 2003/0125986 A1 | 7/2003 | Collosi |
| 2003/0130875 A1 | 7/2003 | Hawash et al. |
| 2003/0149594 A1 | 8/2003 | Beazley et al. |
| 2003/0149625 A1 | 8/2003 | Leonardi et al. |
| 2003/0154163 A1 | 8/2003 | Phillips et al. |
| 2003/0229519 A1* | 12/2003 | Eidex et al. ............ 705/2 |
| 2003/0229540 A1 | 12/2003 | Algiene |
| 2004/0006490 A1 | 1/2004 | Gingrich et al. |
| 2004/0019464 A1 | 1/2004 | Martucci et al. |
| 2004/0039599 A1 | 2/2004 | Fralic |
| 2004/0046020 A1 | 3/2004 | Andreasson et al. |
| 2004/0054657 A1 | 3/2004 | Takeyama |
| 2004/0073457 A1 | 4/2004 | Kalies |
| 2004/0078234 A1 | 4/2004 | Tallal |
| 2004/0093242 A1 | 5/2004 | Cadigan et al. |
| 2004/0107117 A1 | 6/2004 | Denny |
| 2004/0111277 A1 | 6/2004 | Pearson et al. |
| 2004/0111291 A1 | 6/2004 | Dust et al. |
| 2004/0117323 A1 | 6/2004 | Mindala |
| 2004/0133452 A1* | 7/2004 | Denny et al. ............ 705/2 |
| 2004/0148198 A1 | 7/2004 | Kalies |
| 2004/0153336 A1 | 8/2004 | Virdee et al. |
| 2004/0172281 A1 | 9/2004 | Stanners |
| 2004/0188998 A1 | 9/2004 | Henthorn |
| 2004/0249745 A1 | 12/2004 | Baaren |
| 2005/0015280 A1 | 1/2005 | Gabel et al. |
| 2005/0033604 A1 | 2/2005 | Hogan |
| 2005/0033610 A1 | 2/2005 | Cunningham |
| 2005/0033736 A1 | 2/2005 | Carlin et al. |

(56) References Cited

U.S. PATENT DOCUMENTS

| | | | |
|---|---|---|---|
| 2005/0060201 A1 | 3/2005 | Connely, III et al. | |
| 2005/0065821 A1 | 3/2005 | Kalies | |
| 2005/0086081 A1 | 4/2005 | Brock-Fisher | |
| 2005/0090425 A1 | 4/2005 | Reardan et al. | |
| 2005/0102169 A1 | 5/2005 | Wilson | |
| 2005/0125292 A1 | 6/2005 | Kassab et al. | |
| 2005/0154627 A1 | 7/2005 | Zuzek et al. | |
| 2005/0171815 A1 | 8/2005 | Vanderveen | |
| 2005/0187793 A1 | 8/2005 | Myles | |
| 2005/0197862 A1 | 9/2005 | Paterson et al. | |
| 2005/0240473 A1 | 10/2005 | Ayers, Jr. et al. | |
| 2005/0261944 A1 | 11/2005 | Rosenberger | |
| 2005/0288972 A1 | 12/2005 | Marvin et al. | |
| 2006/0015518 A1 | 1/2006 | Eletreby et al. | |
| 2006/0020514 A1 | 1/2006 | Yered | |
| 2006/0026041 A1 | 2/2006 | Ullman | |
| 2006/0085230 A1 | 4/2006 | Brill et al. | |
| 2006/0149587 A1 | 7/2006 | Hill, Sr. et al. | |
| 2006/0149784 A1 | 7/2006 | Tholl et al. | |
| 2006/0184391 A1 | 8/2006 | Barre et al. | |
| 2006/0212318 A1* | 9/2006 | Dooley et al. | 705/4 |
| 2006/0224415 A1 | 10/2006 | Hudson et al. | |
| 2006/0229915 A1 | 10/2006 | Kosinski et al. | |
| 2006/0247948 A1 | 11/2006 | Ellis et al. | |
| 2006/0259363 A1 | 11/2006 | Jhetam et al. | |
| 2006/0271398 A1 | 11/2006 | Belcastro | |
| 2006/0271405 A1 | 11/2006 | Cipolle et al. | |
| 2006/0287886 A1 | 12/2006 | Kitazawa | |
| 2007/0005402 A1 | 1/2007 | Kennedy et al. | |
| 2007/0050209 A1 | 3/2007 | Yered | |
| 2007/0088576 A1 | 4/2007 | de Beus et al. | |
| 2007/0124177 A1 | 5/2007 | Engleson et al. | |
| 2007/0136100 A1 | 6/2007 | Daugherty et al. | |
| 2007/0162433 A1* | 7/2007 | Peters | 707/3 |
| 2007/0179957 A1 | 8/2007 | Gibson et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2008/0033750 A1 | 2/2008 | Burriss et al. | |
| 2010/0211414 A1 | 8/2010 | Tholl et al. | |

FOREIGN PATENT DOCUMENTS

| | | |
|---|---|---|
| WO | 9106917 A1 | 5/1991 |
| WO | 9503569 A3 | 2/1995 |
| WO | 9725682 A1 | 7/1997 |
| WO | 9850871 A1 | 11/1998 |
| WO | 0039737 A1 | 7/2000 |
| WO | 2007025295 A2 | 3/2007 |

OTHER PUBLICATIONS

Non-final Office Action for U.S. Appl. No. 12/345,800 mailed Mar. 29, 2011.

Final Office Action for U.S. Appl. No. 12/345,800 mailed Sep. 14, 2011.

Final Office Action for U.S. Appl. No. 12/164,898 mailed May 26, 2011.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-32. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005. URL: http://www.awarix.com.

Non-Final Office Action for U.S. Appl. No. 12/751,156 mailed Aug. 1, 2012.

Final Office Action for U.S. Appl. No. 12/751,156 mailed Nov. 30, 2012.

Non-Final Office Action for U.S. Appl. No. 12/751,156 mailed Mar. 22, 2013.

* cited by examiner

FIGURE 5

TransAnalyzer - Microsoft Internet Explorer — 500

File  Edit  View  Favorites  Tools  Help

))((  RelayHealth

Transaction Performance Monitor
Transaction Analyzer

[Logout] [Help!] [Home] [Save!]

502 — InBound ○
504 — OutBound ● [OUTBD3 ▽] — 506

Report Type
[Status History ▽] — 508

| From | 09/05/07 ▽ |
| To | 09/05/07 ▽ |

Day: 09/05/07 ▽

Hour: [10 ▽] [11 ▽]

Minute: [25 ▽] [25 ▽]

Increment: [5~10 ▽] [Submit]

Related Bin

| 999991 | 999992 | 999993 | 999994 | 999995 | 999996 | 999997 | 999998 | 999999 |

Outbound OUTBD3 Status History Report — 510

| Date » | Time » | Trans | Resp | Timeouts | Tout% | Rejects | Rej % | Reversals | Rev % | Rejects Analysis |
|---|---|---|---|---|---|---|---|---|---|---|
| 09/05/07 | 11:10:00 | 29 | 2.41 | 1 | 3.45 | 2 | 6.90 | 6 | 20.69 | Analyze [25]1[70]1[99]1 |
| 09/05/07 | 11:05:00 | 15 | 2.95 | 1 | 6.67 | 3 | 20.00 | 3 | 20.00 | Analyze [09]2[70]1[92]1 |
| 09/05/07 | 11:00:00 | 8 | 2.72 | 0 | 0.00 | 3 | 37.50 | 1 | 12.50 | Analyze [09]3 |
| 09/05/07 | 10:55:00 | 14 | 2.43 | 0 | 0.00 | 2 | 14.29 | 2 | 14.29 | Analyze [70]2 — 512 |
| 09/05/07 | 10:50:00 | 26 | 3.32 | 1 | 3.85 | 0 | 0.00 | 4 | 0.00 | Analyze [99]1 |
| 09/05/07 | 10:45:00 | 33 | 3.48 | 3 | 9.09 | 0 | 0.00 | 5 | 0.00 | Analyze [99]3 |
| 09/05/07 | 10:40:00 | 24 | 3.44 | 3 | 12.50 | 1 | 4.35 | 5 | 4.35 | Analyze [99]3 |
| 09/05/07 | 10:35:00 | 23 | 2.56 | 0 | 0.00 | 3 | 20.00 | 1 | 20.00 | Analyze [70]1 |
| 09/05/07 | 10:30:00 | 15 | 3.14 | 0 | 0.00 | 1 | 4.35 | 7 | 4.35 | Analyze [52]1[76]1[79]1 |
| 09/05/07 | 10:25:00 | 23 | 2.44 | 0 | 0.00 | 1 | 4.35 | 7 | 4.35 | Analyze [76]1 |

© Internet

RejByBin - Microsoft Internet Explorer

File  Edit  View  Favorites  Tools  Help

RelayHealth  Transaction Performance Monitor  [Logout] [Home] [Help!] [Save!]
Error Code Bin Cross Analyzer Error Code [25] = M/I Prescriber ID
Bin Cross Analysis
Select [ 25 ▽ ]   From [09/05/07 ▽] [11 ▽] [05 ▽] To [09/05/07 ▽] [11 ▽] [10 ▽] [Submit]

Total Transactions = 224 Total Rejects = 91 Total Rejects pct = 40.63%

| Bin | Name | Rejects ≫ | Total Trans | % of Total Trans | Total Rejects | % of Total Rejects |
|---|---|---|---|---|---|---|
| 999991 | Payer A | 5 | 342 | 1.462 | 62 | 8.065 |
| 999992 | Payer B | 5 | 1189 | 0.421 | 181 | 2.762 |
| 999993 | Payer C | 2 | 92 | 2.174 | 8 | 25.000 |
| 999994 | Payer D | 2 | 733 | 0.273 | 118 | 1.695 |
| 999995 | Payer E | 2 | 226 | 0.885 | 70 | 2.857 |
| 999996 | Payer F | 1 | 137 | 0.730 | 30 | 3.333 |
| 999997 | Payer G | 1 | 43 | 2.326 | 11 | 9.091 |
| 999998 | Payer H | 1 | 355 | 0.282 | 47 | 2.128 |
| 999999 | Payer I | 1 | 457 | 0.219 | 52 | 1.923 |
| 999910 | Payer J | 1 | 126 | 0.794 | 24 | 4.167 |
| 999911 | Payer K | 1 | 15 | 6.667 | 5 | 20.000 |

FIGURE 7

SYSTEMS AND METHODS FOR REAL-TIME MONITORING AND ANALYSIS OF PRESCRIPTION CLAIM REJECTIONS

FIELD OF THE INVENTION

The invention generally relates to prescriptions, and more particularly, to systems and methods for real-time monitoring and analysis of prescription claim rejections.

BACKGROUND OF THE INVENTION

In a conventional prescription claim billing process, a payor/processor may return a particular claim to a pharmacy as a reject. Rejects may be anomalies or there may be a global issue that causes an abnormally high occurrence of rejects. The global issue may be with the payor/processor or with the pharmacy. These types of issues typically require manual intervention for resolution, which can be time consuming and expensive. For instance, if conventional processes are followed, it may take an inordinate amount of time and a relatively high number of similar rejects to notify each relevant party of the associated issue or reason for the reject. In some instances, identification of an issue or reason for the reject may be based on anecdotal evidence which may not be timely or an accurate indicator of the issue or reason for the reject. This may result in the reject of many other or subsequent prescriptions claims and customers may not be accommodated in a timely manner.

Therefore, a need exists for systems and methods for real-time monitoring and analysis of prescription claim rejections.

In addition, a need exists for systems and methods for a transaction performance monitoring system for facilitating the real-time monitoring of the rejection of prescription claims.

Therefore, a need exists for systems and methods for a transaction performance monitoring application for facilitating real-time monitoring and analysis of rejections of prescription claims communicated between at least one dispenser and at least one payor.

SUMMARY OF THE INVENTION

Embodiments of the invention can provide some or all of the above needs. Embodiments of the invention can provide systems and methods for real-time monitoring and analysis of prescription claim rejections. Moreover, embodiments of the invention can provide systems and methods for a transaction performance monitoring system for facilitating real-time monitoring of the rejection of prescription claims. In addition, embodiments of the invention can provide systems and methods for a transaction performance monitoring application for facilitating real-time monitoring and analysis of the rejections of prescription claims communicated between at least one dispenser and at least one payor.

In one embodiment, a transaction performance monitoring system for facilitating real-time monitoring of the rejection of prescription claims can be provided. The transaction performance monitoring system can include a transaction performance monitoring application operable to receive a plurality of claims associated with at least one dispenser, wherein each of the claims relates to at least one prescription and at least one payor. In addition, a transaction performance monitoring application operable to, in real-time, identify rejected claims and associated causes of the rejected claims. Furthermore, a transaction performance monitoring system can include a network operable to communicate the plurality of claims between the at least one dispenser and the at least one payor.

In accordance with another embodiment of the invention, a method for facilitating real-time monitoring of the rejection of prescription claims communicated between at least one dispenser and at least one payor can be implemented. The method can include receiving a plurality of claims associated with at least one dispenser, wherein each of the claims relates to at least one prescription and at least one payor. In addition, the method can include identifying, in real-time, rejected claims and associated causes of the rejected claims. Furthermore, the method can include outputting a real-time display of aggregated rejected claims and associated causes of the rejected claims.

In another embodiment, a transaction performance monitoring application for facilitating the real-time monitoring of the rejection of prescription claims communicated between at least one dispenser and at least one payor via a network can be implemented. The transaction performance monitoring application can include computer-readable instructions operable to receive a plurality of claims associated with at least one dispenser, wherein each of the plurality of claims relates to at least one prescription and at least one payor. In addition, the computer-readable instructions can be operable to, in real-time, identify rejected claims and associated causes of the rejected claims. Further, the computer-readable instructions can be operable to determining at least one NCPDP (National Council for Prescription Drug Programs) reject code associated with each rejected claim. Furthermore, the computer-readable instructions can be operable to provide a user interface for monitoring, in real-time, rejected claims and the associated causes of the rejected claims. Moreover, the computer-readable instructions can be operable to communicate at least a portion of the plurality of claims between the at least one dispenser and the at least one payor.

Other systems and processes according to various embodiments of the invention will become apparent with respect to the remainder of this document.

BRIEF DESCRIPTION OF THE DRAWINGS

Reference will now be made to the accompanying drawings, which are not necessarily drawn to scale, and wherein:

FIGS. 3-7 are example screenshots illustrating example systems and methods in accordance with embodiments of the invention.

DETAILED DESCRIPTION OF EMBODIMENTS OF THE INVENTION

The invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will convey the scope of the invention. Like numbers refer to like elements throughout.

As used herein, the terms "dispenser", "provider", "pharmacy", "subscriber", and their respective pluralized forms are used interchangeably throughout the description, and should be construed to cover any dispenser or provider of a prescription drug or substance.

The terms "transaction", "claims transaction", "claim transaction", "claim", "prescription claim", "drug claim", and their respective pluralized forms are used interchangeably throughout the description, and should be construed to cover any form of data associated with a drug purchase on behalf of a customer or patient.

The term "payor", "claim processor", "payor/processor", "insurance company", and their respective pluralized forms are interchangeably used throughout the description, and should be construed to cover any entity that reimburses any portion of a cost to a customer, patient, dispenser, provider, or other entity submitting a claim for reimbursement.

The terms "real-time" and "near real-time" are interchangeably used throughout the description, and should be construed to mean processing, updating, or reacting to data at the same or approximately the same rate as data is received.

The term "computer-readable medium" describes any form of memory or a propagated signal transmission medium. Propagated signals representing data and computer-executable instructions can be transferred between network devices and systems.

The term "interface" should be construed to mean a communication link between a claims switch and another system, for instance, a client system or a payor/processor system.

Figure 1:
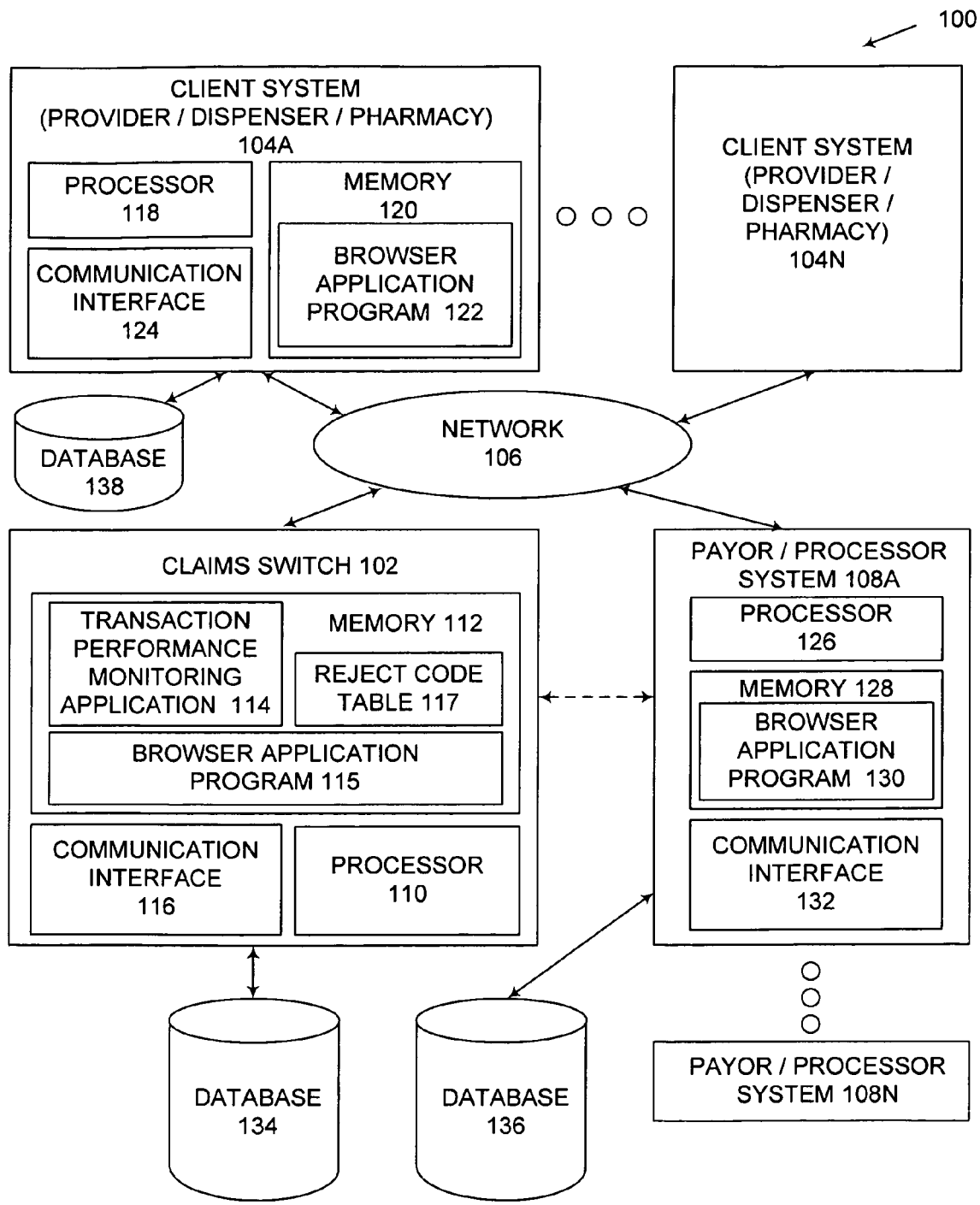
FIG. 1 illustrates an example system in accordance with an embodiment of the invention.

FIG. 1 illustrates an example system in accordance with an embodiment of the invention. In this example, a transaction performance monitoring system 100 can include a claims switch 102 in communication with one or more client systems 104A-104N via at least one network 106, or via one or more separate networks. Client systems 104A-N are typically associated with at least one dispenser or provider, for example, a pharmacy. In addition, the transaction performance monitoring system 100 can also be in communication with at least one payor/processor system 108A-N via the at least one network 106, or via one or more separate networks. Payor/processor systems are typically associated with at least one payor or processor, for example, an insurance company. In the example shown in FIG. 1, the transaction performance monitoring system 100 can monitor, analyze, and process one or more transactions, such as prescription claim transactions, via a real-time claims network. The transaction performance monitoring system 100 and associated components are shown by way of example, and in other embodiments, similar or different components, data inputs, and data outputs may exist.

The claims switch 102 can be a switch operable to handle and process one or more claim transactions, such as prescription claims and drug claims. In one embodiment, a claims switch 102 can be a server, multiple servers, or any number of processor-based devices. The claims switch 102 is further operable to receive one or more claims transactions from any number of client systems 104A-104N. Transactions received by the claims switch 102 can also include claims submitted by one or more client systems, such as 104A-104N. As shown in FIG. 1, a claims switch 102 can include a processor 110, a memory 112 with a transaction performance monitoring application 114, a browser application program 115, and a communication interface 116. The processor 110 can be operable to execute the transaction performance monitoring application 114, a browser application program 115 and/or other sets of computer-executable instructions stored in the memory 112. In other embodiments, the processor 110 can be operable to access and read various associated computer-readable media having stored thereon data and/or computer-executable instructions for implementing certain methods according to embodiments of the invention. The communication interface 116 can be operable to receive input from a user, generate an output for the user, and communicate with one or more client systems 104A-104N and one or more payor/processor systems 108A-N. In some embodiments, a claims switch 102 can include various input/output (I/O) devices, such as a keyboard, mouse, printer, microphone, speaker, monitor, bar code readers/scanners, RFID readers, and the like. Furthermore, in some embodiments, a communication interface 116 may take any number of forms, such as a network interface card, a modem, a wireless network card, and the like.

A transaction performance monitoring application 114 can implement or otherwise utilize any number of processes, tables, filters, lists, screens, devices or other routines to identify or otherwise select in real-time a portion of the received claims transactions as rejected claims. Examples of processes, tables, filters, lists, screens, devices or other routines can include, but are not limited to, a reject code table such as 117, which may be stored in memory 112 or other associated data storage devices.

In one embodiment, when prescription claims or transactions are transmitted from one or more payor/processor systems 108A-108N, the claim switch 102 can receive the prescription claims or transactions via the network 106. The transaction performance monitoring application 114 can compare or otherwise identify certain data in some or all of the prescription claims or transactions to, for example, a reject code table 117, by which the transaction performance monitoring application 114 can identify which of the received prescription claims or transactions are rejected claims. The transaction performance monitoring application 114 could either identify certain prescription claims or transactions as rejected claims by determining that certain data, for example, a rejection code exists in a prescription claim or transaction. In another instance, the transaction performance monitoring application 114 could either identify certain prescription claims or transactions as rejected claims by comparing whether certain data in a prescription claim or transaction matches a rejection code in the reject code table 117. In either instance, the transaction performance monitoring application 114 can process prescription claims or transactions in real-time or near real-time to identify certain prescription claims or transactions as rejected claims.

In one embodiment, a reject code table 117 can include a predefined list of one or more NCPDP (National Council for Prescription Drug Programs) reject codes, and a corresponding list of associated reject causes. For example, a reject code table can include a list of NCPDP reject codes in one column, and a list of corresponding reject causes corresponding to each of the NCPDP reject codes can be in a second column. In other embodiments, a reject code can be numeric, text, alphanumeric, or any combination of symbols used to indicate a rejected prescription claim or transaction. A corresponding reject cause can be an explanation used to indicate a cause or reason for why a particular prescription claim or transaction has been rejected. Example reject codes can include, but are not limited to, 01, 1C, 28, *95, AA, and 1001. Example corresponding reject causes can include, but are not limited to, missing/invalid BIN number, missing/invalid smoker/non-smoker code, missing/invalid date prescription written, time out, patient spenddown not met, and required segment missing. Other lists, data, or information in a reject code table can exist, and can be compared with reject codes associated with prescription claims or transactions by a transaction performance monitoring application 114.

In certain embodiments, the transaction performance monitoring application 114 may implement one or more different reject code tables for different dispensers or providers 104A-N and/or different payor/processor systems, such as 108A-N.

In one embodiment, a transaction performance monitoring application, such as 114, can be operable to receive a plurality of claims associated with at least one dispenser, wherein each of the claims relates to at least one prescription and at least one payor.

In another embodiment, a transaction performance monitoring application, such as 114, can be operable to receive, from a claims switch, a plurality of claims associated with at least one dispenser, wherein each of the claims relates to at least one prescription and at least one payor.

In one embodiment, a transaction performance monitoring application, such as 114, can provide a user interface that provides insight for a user into the performance of claim transactions traffic through a network, such as network 106, or the RelayHealth Intelligent Network. In certain embodiments, a transaction performance monitoring application, such as 114, can be a web-enabled application or service operable to provide a relatively efficient, secure means to monitor, view, and respond to claim transaction processing status from any number of browser application program-equipped client systems, payor/processors, clients, servers, hosts, systems, or corporate data centers.

In certain embodiments, a transaction performance monitoring application, such as 114, can facilitate viewing claim transaction information in real-time or near real-time. For example, using a transaction performance monitoring application, such as 114, a user can view real-time claim transaction performance data as well as sixty (60) days of historical information about the performance of claim transactions processed by a network, such as network 106 or the RelayHealth Intelligent Network.

In certain embodiments, a transaction performance monitoring application, such as 114, can facilitate centralized or remote monitoring of claims processed through a network, such as network 106 or the RelayHealth Intelligent Network.

In certain embodiments, a transaction performance monitoring application, such as 114, can facilitate real-time or near real-time monitoring of claim transactions processing, and can provide user notifications of predefined claim transaction response levels.

In certain embodiments, a transaction performance monitoring application, such as 114, can facilitate recognition of claim transaction processing issues and problems, and can facilitate immediate addressing of such issues and problems.

In certain embodiments, a transaction performance monitoring application, such as 114, can verify or otherwise validate inbound and outbound claim processing traffic between a plurality of dispensers or providers, a network such as network 106 or the RelayHealth Intelligent Network, and a plurality of payor/processors.

In certain embodiments, a transaction performance monitoring application, such as 114, can provide real-time alerts regarding claim transaction rejects and/or system timeouts via a user interface such as display monitor operable to provide respective color changes for various alerts.

In certain embodiments, a transaction performance monitoring application, such as 114, can facilitate viewing claim transaction reject level information at the interface or BIN level.

In certain embodiments, a transaction performance monitoring application, such as 114, can facilitate user selectable alert thresholds at the interface, BIN or NCPDP reject code level.

In certain embodiments, a transaction performance monitoring application, such as 114, can facilitate analysis of claim transaction performance traffic statistics and associated details at the interface or BIN level.

In certain embodiments, a transaction performance monitoring application, such as 114, can facilitate one or more user reports, for instance, user downloads of displayed claim transaction performance information via an output format such as a CSV-type (comma separated values) file.

Although a single transaction performance monitoring application 114 is shown at the claims switch 102 in FIG. 1, other embodiments may have multiple instances of transaction performance monitoring applications similar to 114. Such embodiments can include hosting other transaction performance monitoring applications similar to 114 in various system components including, but not limited to, one or more client systems 104A-104N, components associated with the network 106, or one or more payor/processor systems 108A-N.

A transaction performance monitoring application, such as 114, may operate in conjunction with, may include additional instructions, or otherwise access other application program modules for performing other pre-processing or post-processing methods described herein. One may appreciate that the claims switch 102 may include alternate and/or additional components, hardware or software.

In one embodiment, a transaction performance monitoring application, such as 114, can include computer-readable instructions or computer code operable to receive a plurality of claims associated with at least one dispenser, wherein each of the plurality of claims relates to at least one prescription and at least one payor. In addition, such computer-readable instructions or computer code can be operable to, in real-time, identify rejected claims and associated causes of the rejected claims. Furthermore, such computer-readable instructions or computer code can be operable to determine at least one NCPDP (National Council for Prescription Drug Programs) reject code associated with each rejected claim. Further, such computer-readable instructions or computer code can be operable to provide a user interface for monitoring, in real-time, rejected claims and the associated causes of the rejected claims. Moreover, such computer-readable instructions or computer code can be operable to communicate at least a portion of the plurality of claims between the at least one dispenser and the at least one payor.

In one embodiment, a transaction performance monitoring application can include computer-readable instructions or computer code operable to provide a real-time status of aggregated rejected claims and the associated causes of the rejected claims.

In one embodiment, a transaction performance monitoring application can include computer-readable instructions or computer code operable to in-real-time, identify rejected claims and associated causes of the rejected claims based at least in part on determining at least one respective rejection code associated with each of the rejected claims.

In one embodiment, a transaction performance monitoring application can include computer-readable instructions or computer code operable to provide a user interface for setting at least one alert triggered by a predefined percentage or number of rejected claims at a predefined level.

In one embodiment, a predefined level comprises at least one of the following: interface level, BIN level, reject code level, reject code level within an interface, or reject code level within a BIN.

In one embodiment, a transaction performance monitoring application can include computer-readable instructions or computer code operable to output at least one report comprising real-time data associated with rejected claims and associated causes of the rejected claims.

The network 106 can be any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 106 may also allow for any combination of real-time, near real-time, off-line, and/or batch transactions to be transmitted between the claims switch 102, client systems 104A-104N, and payor/processor systems 108A-N. Due to network connectivity, various methodologies as described herein may be practiced in the context of distributed computing environments. Although the client systems 104A-104N and payor/processor systems 108A-N are shown for simplicity as being in communication with the claims switch 102 via one intervening network 106, it is to be understood that any other network configuration is possible. For example, intervening network 106 may include a plurality of networks, each with devices such as gateways and routers for providing connectivity between or among any number of networks. Instead of or in addition to a network 106 dedicated communication links may be used to connect the various components or devices of embodiments of the invention. In one example, a dedicated communication link can be used to facilitate relatively secure data transmission between any number of the client systems 104A-N and the claims switch 102, or alternatively, between the claims switch 102 and any number of the payor/processor systems 108A-N.

Each of the client systems, such as 104A-104N, can be administered by a respective dispenser or provider, for example a pharmacy, as described above. In one embodiment, each of the client systems 104A-104N can be any processor-driven device, such as a personal computer, laptop computer, handheld computer, or mainframe computer. As shown in FIG. 1, a client system, such as 104A can include a processor 118, a memory 120 with a browser application program 122, and a communication interface 124. The processor 118 can be operable to execute the browser application program 122 or other set of computer-executable instructions stored in the memory 120. In other embodiments, the processor 118 can be operable to access and read various associated computer-readable media having stored thereon data and/or computer-executable instructions for implementing methods according to embodiments of the invention. The communication interface 124 can be operable to receive input from a user, generate an output for the user, and communicate with the claims switch 102 and one or more payor/processor systems 108A-N as needed. For example, the browser application program 122 may include or otherwise facilitate access to the network 106 by way of other software, including a dedicated program, for interacting with the claims switch 102 and/or transaction performance monitoring application 114. In one embodiment, a user, such as a pharmacist or other pharmacy employee, may utilize the browser application program 122 in preparing and providing a prescription drug request or order to the claims switch 102 for processing. The browser application program 122 can be utilized to retrieve or otherwise receive data from the claims switch 102, including pricing and discount information for the prescription drug request or order. In some embodiments, client systems 104A-104N can include various input/output (I/O) devices, such as a keyboard, mouse, printer, microphone, speaker, monitor, bar code readers/scanners, RFID readers, and the like. Furthermore, in some embodiments, a communication interface 124 may take any number of forms, such as a network interface card, a modem, a wireless network card, and the like. The client systems 104A-104N may include additional instructions or access other program modules for performing other pre-processing or post-processing methods described herein. One may appreciate that the client systems 104A-104N may include alternate and/or additional components, hardware or software.

As described above, each of the payor/processor systems 108A-108N can be administered by a respective payor, payor/processor, insurance company, or any entity that reimburses any portion of a cost to a customer, patient, dispenser, provider, or other entity submitting a claim for reimbursement. As shown in FIG. 1, each payor/processor system, such as 108A, can include a processor 126, a memory 128 with a browser application program 130, and a communication interface 132. The processor 126 can be operable to execute the browser application program 130 or other set of computer-executable instructions stored in the memory 128. In the embodiment shown, the browser application program 130 can receive selected data from claims transactions from the claims switch 102. In one embodiment, the browser application program 130 can perform some or all of the functionality described with respect to the browser application program 122 associated with the client systems 104A-104N. In other embodiments, the processor 126 can be operable to access and read various associated computer-readable media having stored thereon data and/or computer-executable instructions for implementing methods according to embodiments of the invention. The communication interface 132 can be operable to receive input from a user, generate an output for the user, and communicate with the claims switch 102 and any number of the client systems 104A-104N as needed. For example, the browser application program 130 may include or otherwise facilitate access to the network 106 by way of other software, including a dedicated program, for interacting with the claims switch 102 and/or transaction performance monitoring application 114. In some embodiments, a payor/processor system, such as 108A, can include various input/output (I/O) devices, such as a keyboard, mouse, printer, microphone, speaker, monitor, bar code readers/scanners, RFID readers, and the like. Furthermore, in some embodiments, a communication interface 132 may take any number of forms, such as a network interface card, a modem, a wireless network card, and the like. The payor/processor systems 108A-108N may include additional instructions or access other program modules for performing other pre-processing or post-processing methods described herein. One may appreciate that the payor/processor systems 108A-108N may include alternate and/or additional components, hardware or software.

As illustrated in FIG. 1, the claims switch 102 may include or be in communication with at least one data storage device, such as database 134. If the claims switch 102 includes a data storage device, then the data storage device could also be part of the memory 112. The data storage device or database 134 and/or memory 112 may store, for example, previously received transactions and associated data, selected or rejected claim transactions and associated data, and any number of business rules, filters, or screens for processing transactions. Although a single data storage device or database 134 is referred to herein for simplicity, one will appreciate that multiple physical and/or logical data storage devices or databases may be used to store the above mentioned data. For security and performance purposes, the claims switch 102 may have a dedicated connection to the data storage device or database 134, as shown. However, the claims switch 102 may also communicate with the data storage device or database 134 via a network 106. In other embodiments of the invention, the claims switch 102 may include the data storage device or database 134 locally. The claims switch 102 may also otherwise be part of a distributed or redundant database management system (DBMS).

Similar to the claims switch 102, some or all of the payor/processor systems 108A-108N may include or be in communication with at least one data storage device or database 136 with similar functionality to database 134. In addition, some or all of the client systems 104A-104N may include or be in communication with at least one data storage device or database 138 with similar functionality to database 134.

One will appreciate that components of the system 100 shown in and described with respect to FIG. 1 are provided by way of example only. Numerous other operating environments, system architectures, and device configurations are possible. Accordingly, embodiments of the invention should not be construed as being limited to any particular operating environment, system architecture, or device configuration.

Embodiments of a system, such as 100, can facilitate real-time monitoring and analysis of prescription claim rejections. Furthermore, embodiments of a system, such as 100, can facilitate real-time monitoring and analysis of the rejections of prescription claims communicated between at least one dispenser and at least one payor. In addition, embodiments of a system, such as 100, can facilitate real-time monitoring and analysis of the rejections of prescription claims communicated between at least one dispenser and at least one payor via a network. Example operations of a system, such as 100 of FIG. 1, and its various components as well as associated methods and processes are described by reference to FIG. 2.

Figure 2:
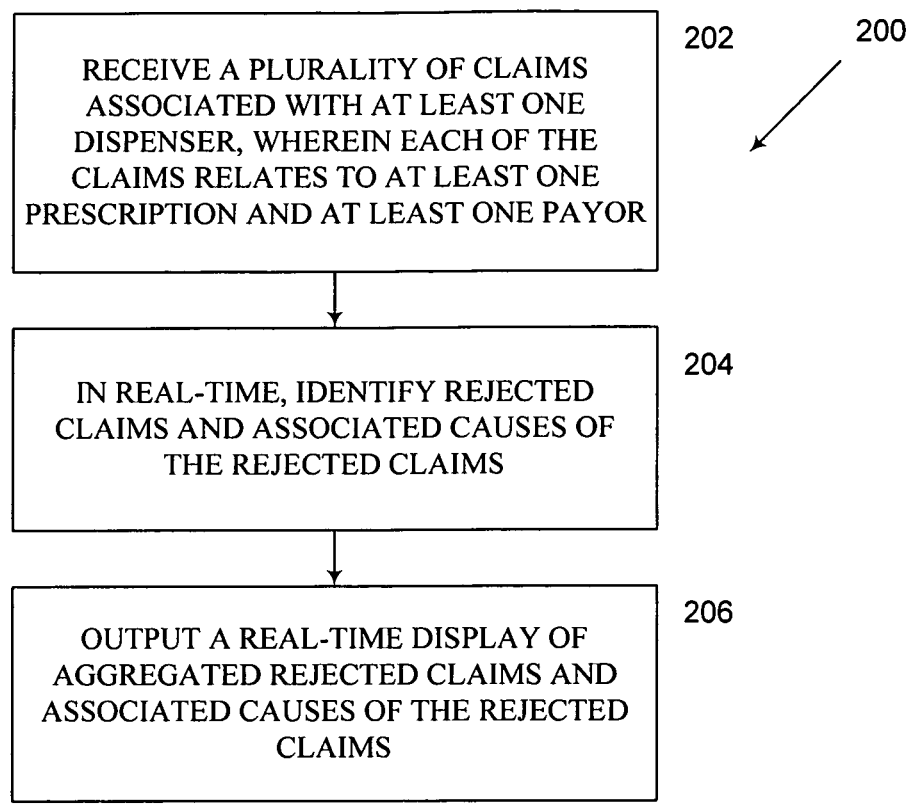
FIG. 2 illustrates an example method in accordance with an embodiment of the invention.

FIG. 2 is a process flowchart illustrating an example method in accordance with embodiments of the invention. The example method 200 shown in FIG. 2 provides a method for real-time monitoring and analysis of rejections of claims communicated between at least one dispenser and at least one payor. The method 200 can be implemented by a system, such as 100 of FIG. 1.

The method 200 begins at block 202. In block 202, a plurality of claims associated with at least one dispenser is received, wherein each of the claims relates to at least one prescription and at least one payor. For example, as shown in FIG. 1, one or more prescription claims or transactions associated with at least one prescription and at least one payor and originating at a client system, such as 104A, can be received by a claims switch 102 or transaction performance monitoring application 114. In another example, one or more prescription claims or transactions associated with at least one prescription and at least one payor and returned by a payor/processor, such as 108A, can be received by a claims switch 102 or transaction performance monitoring application 114. In any instance, a transaction performance monitoring application 114 associated with the claims switch 102 can process some or all of the received prescription claims or transactions.

Block 202 is followed by block 204, in which rejected claims and associated causes of the rejected claims are identified in real-time. In one embodiment, a transaction performance monitoring application 114 can implement in real-time one or more processes, filters, screens, devices, or other routines to identify some or all rejected prescription claims or transactions at a claim switch 102, and to further identify associated causes of the rejected claims. In this example, a reject code table 117 can be implemented by the transaction performance monitoring application 114 to identify or otherwise select rejected prescription drug claims or transactions in real-time. In any instance, the transaction performance monitoring application 114 can, in real-time, identify or otherwise select one or more rejected prescription claims or claim transactions and associated causes of the rejected claims.

In one embodiment, identifying rejected claims and associated causes of the rejected claims includes determining at least one respective rejection code associated with each of the rejected claims.

In one embodiment, identifying rejected claims and associated causes of the rejected claims comprises determining at least one NCPDP (National Council for Prescription Drug Programs) reject code associated with each rejected claim.

In one embodiment, the method 200 further includes setting at least one alert triggered by a predefined percentage or number of rejected claims at a predefined level.

In one embodiment, a predefined level includes at least one of the following: interface level, BIN level, reject code level, reject code level within an interface, or reject code level within a BIN.

Block 204 is followed by block 206, wherein a real-time display of aggregated rejected claims and associated causes of the rejected claims is output. In this embodiment, as shown in FIG. 1, the transaction performance monitoring application 114 can facilitate a real-time display or output of identified or otherwise selected rejected prescription claims or transactions. As discussed above, the transaction performance monitoring application 114 can, in real-time, identify or otherwise select rejected prescription claims or transactions and associated causes of the rejected claims. The transaction performance monitoring application 114 can aggregate some or all of the rejected claims and associated causes of the rejected claims in a data storage device or memory, such as 112. The transaction performance monitoring application 114 can generate an output for display of some or all of the rejected claims and associated causes of the rejected claims for transmission via a communication interface, such as 116. In one example, a transaction performance monitoring application 114 can format and display some or all of the rejected claims and associated causes of the rejected claims. In this example, the transaction performance monitoring application 114 can output any number of real-time displays via the communication interface 116, such as an output to a display monitor. The example screenshots in FIGS. 3-7 described below represent example outputs of real-time displays to a display monitor.

In one embodiment, a display further includes at least one of the following: summary information associated with a specific interface, one or more user specified parameters, a rejected claim total for a defined time period, or a status history associated with aggregated rejected claims.

Other example outputs of a real-time display can be printed on a medium such as electronic or regular paper, graphical or visual indications, audio indications, or any other output operable to convey data associated with some or all of the rejected claims and associated causes of the rejected claims to a system user. In one embodiment, an output can be CSV-type (comma separated value) file, which can be imported into a variety of application programs for further processing and analysis. Such a file can include, but is not limited to, date, time, transaction numbers, response times, numbers of timeouts, timeout percentages, reject counts, percentages of rejects, reversal counts, percentages of reversals, and other real-time claims or transactions data.

The method 200 of FIG. 2 ends after block 206.

The example elements of FIG. 2 are shown by way of example, and other process embodiments can have fewer or greater numbers of elements, and such elements can be arranged in alternative configurations in accordance with other embodiments of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational elements or steps to be performed on the computer or other programmable apparatus to produce a computer implemented process such that the instructions that execute on the computer or other programmable apparatus provide elements for implementing the functions specified in the flowchart block or blocks.

Accordingly, blocks of the block diagrams and flowchart illustrations support combinations of means for performing the specified functions, combinations of elements or steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements, or combinations of special purpose hardware and computer instructions.

Figure 3:
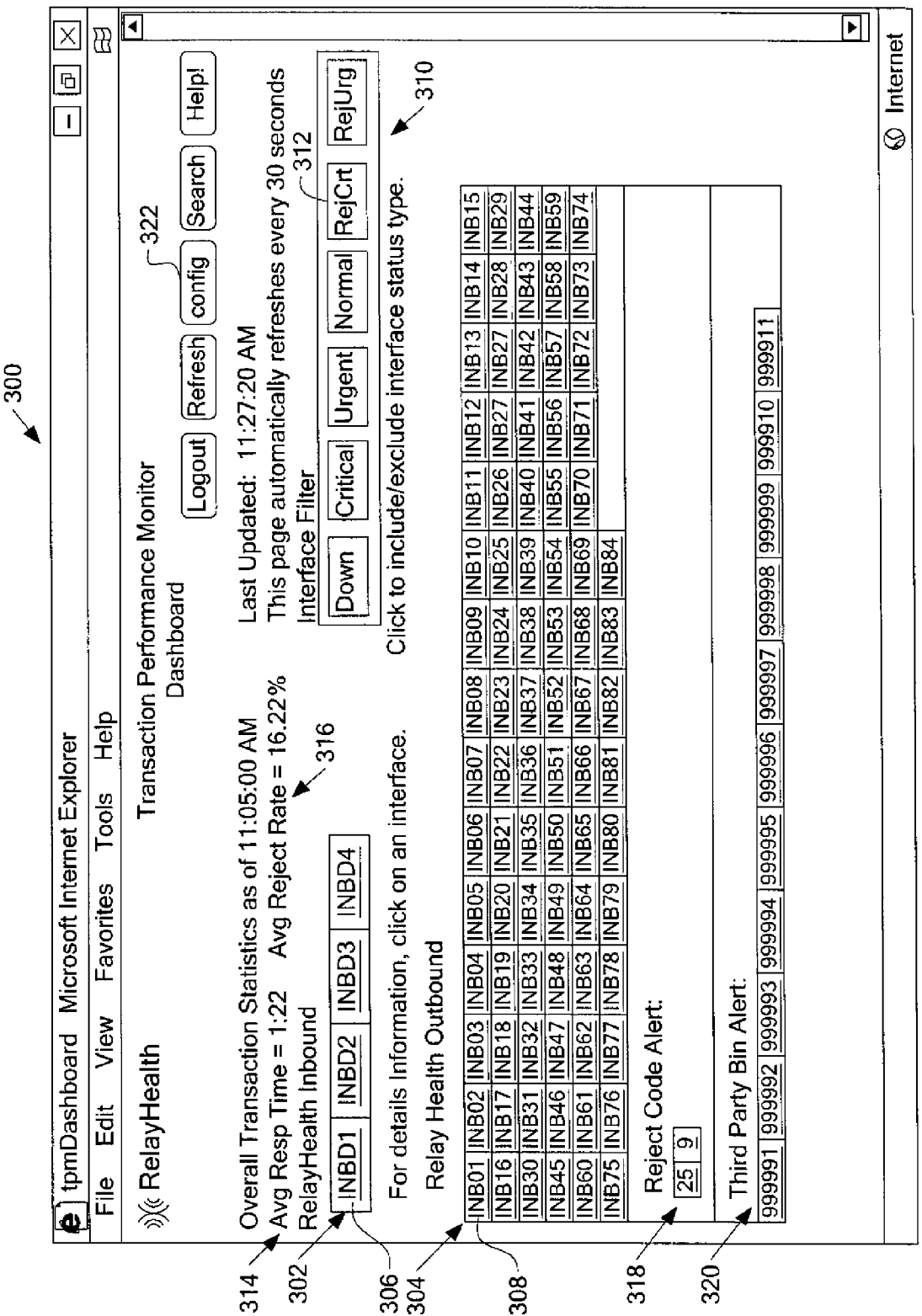

FIGS. 3-7 are example screenshots illustrating example systems and methods in accordance with embodiments of the invention. In FIG. 3, an example screenshot illustrates a user interface 300 or "dashboard" with a real-time display provided by or otherwise facilitated by a transaction performance monitor application, such as 114 in FIG. 1. In this example, the user interface 300 includes a display of real-time inbound and outbound prescription claims or transactions traffic 302, 304 between one or more client systems, such as 104A-104N in FIG. 1, associated with respective dispensers, providers, or pharmacies, a claims switch, such as 102 in FIG. 1, and one or more payor/processor systems, such as 108A-108N in FIG. 1, associated with respective payor/processors. The display as shown in FIG. 3 can be updated in real-time, or in near real-time, by the transaction performance monitor application 114 as needed to reflect new or more recent prescription claims or transactions traffic. A user viewing and implementing the user interface 300 can pinpoint transaction timeouts and unacceptable reject levels. In addition, a user can monitor and analyze traffic statistics at various levels such as the interface, BIN, or reject code level. Furthermore, reduced administrative costs can result since claims monitoring can be centralized for an entity, and a user can quickly recognize and address traffic problems and associated issues.

Each respective indicator for inbound traffic 302, such as INBD1 306, illustrates a particular prescription claim or transaction between at least one client system, such as 104A, and a claims switch, such as 102. Likewise, each respective indicator for outbound traffic 304, such as OUTBD1 308, illustrates a particular prescription claim or transaction between a claims switch, such as 102, and at least one payor/processor system, such as 108A. As new or recent claims or transactions are transmitted via the system 100, the transaction performance monitor application 114 can generate a respective indicator representative of the inbound or outbound status of the particular prescription claim or transaction.

Various functionality can be provided by the user interface 300 shown in FIG. 3 including, but not limited to, filtering status types, viewing distinct color-based status indicators for alerting a user to certain conditions, clickable interfaces to provide additional details, and searching by BIN.

In the embodiment shown in FIG. 3, one or more status type filters 310 can be provided to permit a user to click on or select a particular status type to filter some or all of the prescription claims or transactions, and view only those prescription claims or transactions having a certain status. For example, if a user selected status type filter 312 corresponding to "RejCrt", the transaction performance monitoring application 114 can filter the some or all of the received prescription claims or transactions, and update the user interface 300 to display only those prescription claims or transactions corresponding to the status type filter selected. Example status type filters and corresponding status descriptions and colors can include, but are not limited to, Down=all transactions failed because of a time-out (Red), Critical=50% to 99.99% of transactions failed because of a time-out (Orange), Urgent=5% to 49.99% of the transactions failed because of a time-out, Normal=less than 5% of the transactions failed (Green), RejCrt=above 95% transactions are rejected other than time-outs for more than five consecutive samples (Pink), and RejUrg=above 60% transactions are rejected, other than time-outs for more than five consecutive samples (Yellow). Other filters, colors, and status descriptions can exist in accordance with other embodiments of the invention. In the manner described, a user can, in real-time, view inbound and outbound traffic of prescription claims or transactions via a user interface, such as 300, filter some or all of the traffic, and understand a range of operating efficiencies for the traffic.

In one embodiment, a transaction performance monitoring application 114 can identify whether each received prescription claim or transaction includes a certain reject or response code as described above with respect to FIG. 1. As a percentage of prescription claims or transactions with a particular response code increases, the transaction performance monitor application 114 can generate a change in color of a status indicator, for example, from green to blue to orange to red. Each color may indicate an increase in the number of transactions that return a "time out" reject code. In this example, other types of rejected claims can be indicated separately by either a yellow or pink color status indicator. In this manner, certain outbound traffic indicators 304 can be shown in a certain color depending on the particular reject or response code.

In the embodiment shown in FIG. 3, various transaction statistics for inbound traffic, outbound traffic, or both can be illustrated. For example, an average response time 314 or average transaction time across some or all interfaces can be determined and shown. In another example, an average reject rate 316 or average transaction reject rate across some or all interfaces can be determined and shown. In this manner, a user can, in real-time, view an overall indicator of transaction velocity and reject rate for some or all of the traffic of prescription claims or transactions via a user interface, such as 300.

In the embodiment shown in FIG. 3, clickable interfaces 302, 304, 318, 320, 322 can provide additional details regarding a transaction. For example, a user clicking on a configuration button, such as "CONFIG" 322, can obtain an alert configuration webpage described in detail in FIG. 4 below. In another example, a user clicking on inbound interface 302 or outbound interface 304 can obtain a transaction analyzer webpage described in detail in FIG. 5 below. In another example, a user clicking on a reject code alert interface 318 can obtain an error code BIN cross analyzer webpage described in detail in FIG. 7 below. In another example, a user clicking on a third party BIN alert interface 320 can obtain a transaction analyzer webpage described in detail in FIG. 5 below.

Figure 4:
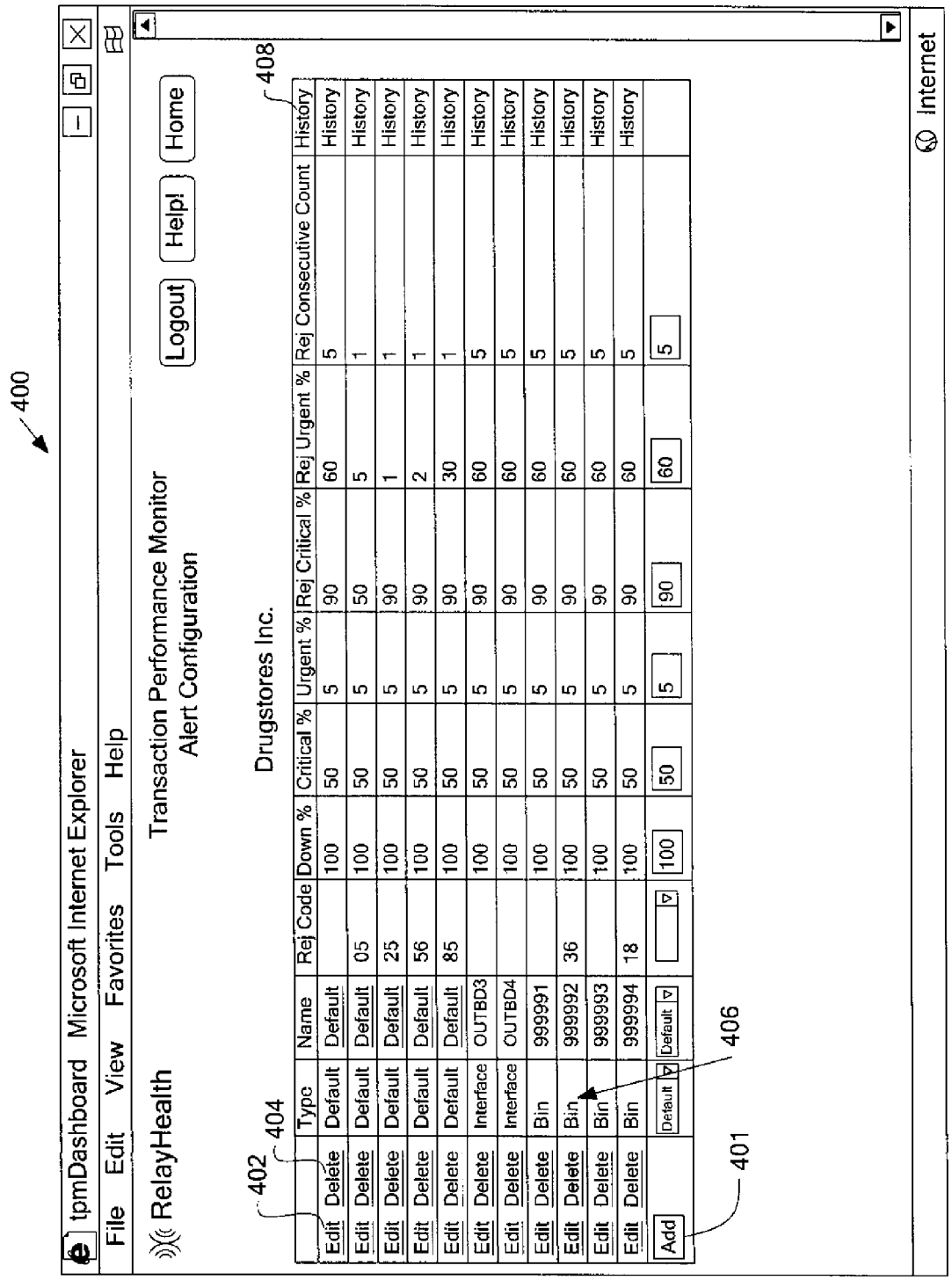

In FIG. 4, an example screenshot illustrates a user interface 400 with a real-time display provided by or otherwise facilitated by a transaction performance monitor application, such as 114 in FIG. 1. In this example, the user interface 400 includes a display of real-time alert configurations for some or all of the interfaces displayed by the user interface 300 of FIG. 3. By way of the add button 401, edit 402 and delete 404 commands, a user can set-up different alerts at various levels including, but not limited to, interface, BIN, reject code, reject code within an interface, and reject code within a BIN. As shown by alert 406, an alert type at a BIN level with a name 99992 for reject code 36 can be set with certain predefined percentages of rejected claims and/or a number of rejected claims at a predefined level. In this manner, a user interface can be provided for setting at least one alert triggered by a predefined percentage or number of rejected claims at a predefined level.

In FIG. 5, an example screenshot illustrates a user interface 500 with a real-time display provided by or otherwise facilitated by a transaction performance monitor application, such as 114 in FIG. 1. In this example, the user interface 500 includes a display of real-time claim or transaction details for some or all of the interfaces displayed by the user interface 300 of FIG. 3. Either inbound or outbound traffic can be analyzed by selecting a respective command 502, 504, or from a list of available interfaces 506. By way of the report type command 508, a user can select different report types including, but not limited to, status history or daily total report types. As shown by field 510, chronologically ordered claims or transactions data can be displayed. In this example, claims or transactions data displayed can include, but is not limited to, number of transactions, response time, number of timeouts, timeout percentage, number of rejects, reject percentage, number of reversals, reversal percentage, and various reject analysis commands, such as "ANALYZE" 512, to provide additional details for particular reject codes. Using a reject analysis command 512, a user can view and sort some or all of details for particular reject codes associated with claims or transactions. A user clicking on a reject analysis command 512 can obtain a reject code analyzer webpage described in detail in FIG. 6 below. In this manner, a user interface can be provided for viewing and obtaining real-time status of aggregated rejected claims and the associated causes of the rejected claims.

Figure 6:
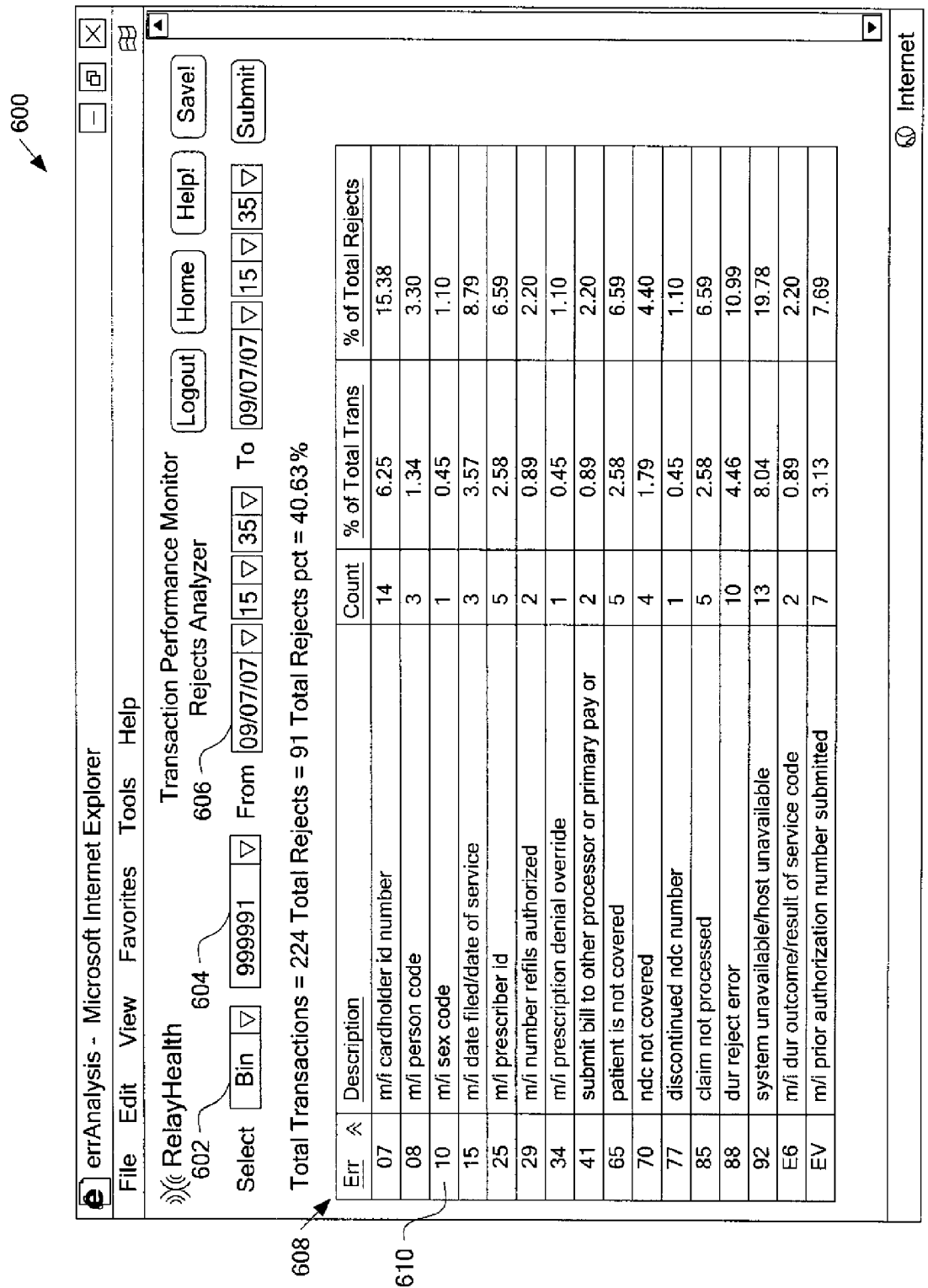

In FIG. 6, an example screenshot illustrates a user interface 600 with a real-time display provided by or otherwise facilitated by a transaction performance monitor application, such as 114 in FIG. 1. In this example, the user interface 600 includes a display of real-time claim or transaction details for some or all of the interfaces displayed by the user interface 300 of FIG. 3. Using a level dropdown command 602, a BIN number selection command 604, and/or a date and time range selection command 606, a user can obtain, display, and sort specific rejected claims or transactions corresponding to the selected levels, BIN number and/or date and time ranges. As shown by field 608, summary total transactions counts, summary total reject counts, summary total rejects percentages, alphanumerically ordered claim rejection codes, corresponding causes for rejection, rejection count numbers, percentages of total transactions, and percentages of total rejects can be displayed and sorted. Using a reject code analysis command, such as a particular reject code 610, a user can view some or all of details for particular reject codes associated with claims or transactions. A user clicking on a reject code analysis command, such as a particular reject code 610, can obtain an error code analyzer webpage with details related to the specific reject code selected. In this manner, a user interface can be provided for viewing and obtaining real-time status of aggregated rejected claims and the associated causes of the rejected claims.

In FIG. 7, an example screenshot illustrates a user interface 700 with a real-time display provided by or otherwise facilitated by a transaction performance monitor application, such as 114 in FIG. 1. In this example, the user interface 700 includes a display of real-time claim or transaction details for some or all of the interfaces displayed by the user interface 300 of FIG. 3. Using an error code dropdown command 702, and/or a date and time range selection command 704, a user can obtain, display, and sort specific rejected claims or transactions by BIN number corresponding to the selected reject codes and/or date and time ranges. As shown by field 706, BIN numbers, payor/processor names, reject counts, total transactions, percentages of total transactions, total reject numbers, and percentage of total rejects can be displayed and sorted. Using BIN selection command 708, a user can view some or all of details for particular BIN numbers associated with rejected claims or transactions. A user clicking on a BIN selection command 708 can obtain the transaction analyzer webpage with details related to the BIN number selected. In this manner, a user interface can be provided for viewing and obtaining real-time status of aggregated rejected claims and the associated causes of the rejected claims.

The screenshots 300, 400, 500, 600, and 700 described above and in FIGS. 3-7 are shown by way of example, and other configurations and functionality associated with a user interface for viewing and obtaining real-time status of aggregated rejected claims and the associated causes of the rejected claims can be provided in accordance with other embodiments of the invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The claimed invention is:

1. A transaction performance monitoring system for facilitating real-time monitoring of the rejection of claims, the transaction performance monitoring system comprising:
   a transaction performance monitoring application operable to:
      receive a plurality of claims associated with at least one dispenser, wherein each of the claims relates to at least one prescription and at least one payor;
      in real-time, identify rejected claims and associated causes of the rejected claims, wherein the rejected claims and associated causes are aggregated to define a total number of rejected claims and a total number for each associated cause; and
      provide a user interface for the at least one payor to monitor inbound and outbound claim traffic in real-time, and to view the total number of rejected claims and total number for each associated cause at an interface level, BIN level, reject code level, reject code level within an interface, or a reject code level within a BIN;
      provide a user interface for setting at least one alert triggered by a predefined percentage of rejected claims or by a predefined number of rejected claims, wherein the rejected claims are at a predefined level comprising at least one of an interface level, BIN level, reject code level within an interface, or reject code within a BIN; and
   a network operable to:
      communicate the plurality of claims between the at least one dispenser and the at least one payor.

2. The system of claim 1, wherein the performance monitoring application is further operable to:
   provide a user interface for monitoring rejected claims and the associated causes of the rejected claims.

3. The system of claim 2, wherein the user interface is operable to provide at least one of the following: summary information associated with a specific interface, one or more user specified parameters, a rejected claim total for a defined time period, or a status history associated with aggregated rejected claims.

4. The system of claim 1, wherein the performance monitoring application is further operable to:
   provide a real-time status of aggregated rejected claims and the associated causes of the rejected claims.

5. The system of claim 1, wherein the performance monitoring application is further operable to:
   in real-time, identify rejected claims and associated causes of the rejected claims based at least in part on determining at least one respective rejection code associated with each of the rejected claims.

6. The system of claim 1, wherein the performance monitoring application is further operable to:
   provide a user interface for setting at least one alert triggered by a predefined percentage or number of rejected claims at a predefined level.

7. The system of claim 6, wherein the predefined level comprises at least one of the following: interface level, BIN level, reject code level, reject code level within an interface, or reject code level within a BIN.

8. The system of claim 1, wherein the performance monitoring application is further operable to:
   output at least one report comprising real-time data associated with rejected claims and associated causes of the rejected claims.

9. A method for facilitating real-time monitoring of the rejection of claims communicated between at least one dispenser and at least one payor, the method comprising:
   receiving, by at least one processor, a plurality of claims associated with at least one dispenser, wherein each of the claims relates to at least one prescription and at least one payor;
   in real-time, identifying, by the at least one processor, rejected claims and associated causes of the rejected claims, wherein the rejected claims and associated causes are aggregated to define a total number of rejected claims and a total number for each associated cause;
   setting at least one alert triggered by a predefined percentage of rejected claims or by a predefined number of rejected claims, wherein the rejected claims are at a predefined level comprising at least one of an interface level, BIN level, reject code level within an interface, or reject code within a BIN; and
   outputting, by the at least one processor, a real-time display of aggregated rejected claims and associated causes of the rejected claims, wherein the at least one payor can monitor inbound and outbound claim traffic in real-time, and view the total number of rejected claims and total number for each associated cause at an interface level, BIN level, reject code level, reject code level within an interface, or a reject code level within a BIN.

10. The method of claim 9, wherein identifying rejected claims and associated causes of the rejected claims comprises determining at least one respective rejection code associated with each of the rejected claims.

11. The method of claim 9, wherein identifying rejected claims and associated causes of the rejected claims comprises determining at least one NCPDP (National Council for Prescription Drug Programs) reject code associated with each rejected claim.

12. The method of claim 9, further comprising:
   setting at least one alert triggered by a predefined percentage or number of rejected claims at a predefined level.

13. The method of claim 12, wherein the predefined level comprises at least one of the following: interface level, BIN level, reject code level, reject code level within an interface, or reject code level within a BIN.

14. The method of claim 9, wherein the display further comprises at least one of the following: summary information associated with a specific interface, one or more user specified parameters, a rejected claim total for a defined time period, or a status history associated with aggregated rejected claims.

15. A transaction performance monitoring application for facilitating real-time monitoring of the rejections of claims communicated between at least one dispenser and at least one payor via a network, the transaction performance monitoring application comprising computer-readable instructions operable to:
   receive a plurality of claims associated with at least one dispenser, wherein each of the plurality of claims relates to at least one prescription and at least one payor;
   in real-time, identify rejected claims and associated causes of the rejected claims, wherein the rejected claims and associated causes are aggregated to define a total number of rejected claims and a total number for each associated cause;
   determining at least one NCPDP (National Council for Prescription Drug Programs) reject code associated with each rejected claim;

provide a user interface for monitoring, in real-time, rejected claims and the associated causes of the rejected claims, wherein the at least one payor can monitor inbound and outbound claim traffic in real-time, and view the total number of rejected claims and total number for each associated cause at an interface level, BIN level, reject code level, reject code level within an interface, or a reject code level within a BIN;

provide a user interface for setting at least one alert triggered by a predefined percentage of rejected claims or by a predefined number of rejected claims, wherein the rejected claims are at a predefined level comprising at least one of an interface level, BIN level, reject code level within an interface, or reject code within a BIN; and communicate at least a portion of the plurality of claims between the at least one dispenser and the at least one payor.

16. The transaction performance monitoring application of claim 15, wherein the computer-readable instructions are further operable to:

provide a real-time status of aggregated rejected claims and the associated causes of the rejected claims.

17. The transaction performance monitoring application of claim 15, wherein the computer-readable instructions are further operable to:

in-real-time, identify rejected claims and associated causes of the rejected claims based at least in part on determining at least one respective rejection code associated with each of the rejected claims.

18. The transaction performance monitoring application of claim 15, wherein the computer-readable instructions are further operable to:

provide a user interface for setting at least one alert triggered by a predefined percentage or number of rejected claims at a predefined level.

19. The transaction performance monitoring application of claim 18, wherein the predefined level comprises at least one of the following: interface level, BIN level, reject code level, reject code level within an interface, or reject code level within a BIN.

20. The transaction performance monitoring application of claim 15, wherein the computer-readable instructions are further operable to:

output at least one report comprising real-time data associated with rejected claims and associated causes of the rejected claims.

* * * * *